(12) United States Patent
D'Agostino

(10) Patent No.: US 8,152,826 B2
(45) Date of Patent: *Apr. 10, 2012

(54) LANCET DEVICE

(75) Inventor: Daniel M. D'Agostino, Watertown, MA (US)

(73) Assignee: Abbott Laboratories, Abbott Park, IL (US)

( * ) Notice: Subject to any disclaimer, the term of this patent is extended or adjusted under 35 U.S.C. 154(b) by 944 days.

This patent is subject to a terminal disclaimer.

(21) Appl. No.: 11/950,204

(22) Filed: Dec. 4, 2007

(65) Prior Publication Data

US 2008/0319469 A1 Dec. 25, 2008

Related U.S. Application Data

(63) Continuation of application No. 10/447,578, filed on May 29, 2003, now Pat. No. 7,303,573.

(51) Int. Cl.
*A61B 17/32* (2006.01)
(52) U.S. Cl. .................... 606/181; 606/182; 606/183
(58) Field of Classification Search .................. 606/181, 606/182, 183, 185; 604/117; 128/770
See application file for complete search history.

(56) References Cited

U.S. PATENT DOCUMENTS

| 5,304,192 A * | 4/1994 | Crouse ........................ 606/181 |
| 5,324,302 A * | 6/1994 | Crouse ........................ 606/181 |
| 6,045,567 A * | 4/2000 | Taylor et al. ................ 606/181 |
| 6,852,119 B1 * | 2/2005 | Abulhaj et al. ............. 606/182 |
| 7,303,573 B2 * | 12/2007 | D'Agostino ................ 606/181 |

FOREIGN PATENT DOCUMENTS

| EP | 1 245 187 | 10/2002 |
| WO | 93/09723 | 5/1993 |
| WO | 01/64105 | 9/2001 |

OTHER PUBLICATIONS

The PCT Search Report (cited in parent U.S. Appl. No. 10/447,578, now U.S. Patent No. 7,303,573).

* cited by examiner

*Primary Examiner* — Vy Q Bui
(74) *Attorney, Agent, or Firm* — Young Basile

(57) ABSTRACT

A lancet device for obtaining a blood sample from a finger or at an alternate site of a patient. The lancet device includes a body and a lancet, the lancet being movable between a retracted position in which the lancet tip is disposed within the body and an extended position in which the lancet tip extends beyond the body. The device is cocked by compressing a U-shaped spring steel accessible on opposite sides of the body, the U-shaped spring steel being coupled to the lancet. Once cocked, a pawl retains the U-shaped spring steel in a compressed state. The device is fired by contacting the patient where sampling is to occur with one end of an actuator, the opposite end of the actuator serving to release the pawl from the U-shaped spring steel.

13 Claims, 10 Drawing Sheets

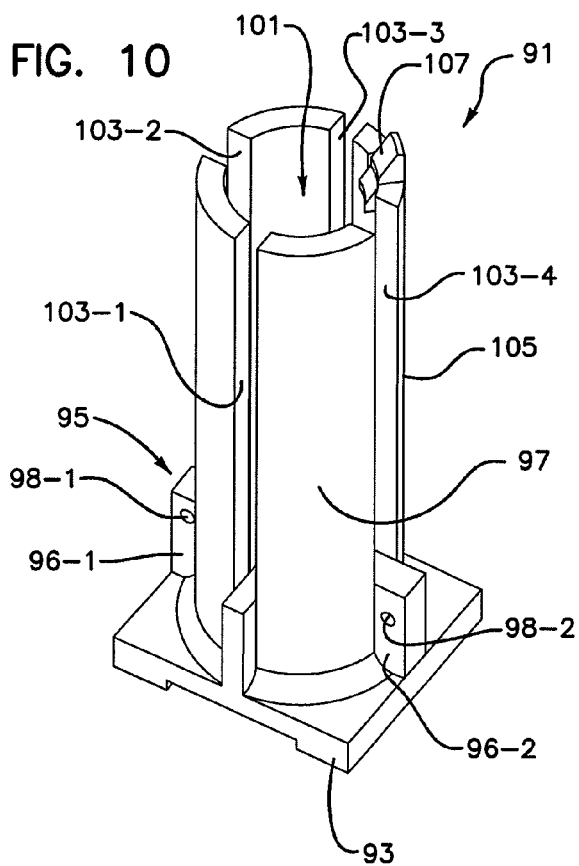
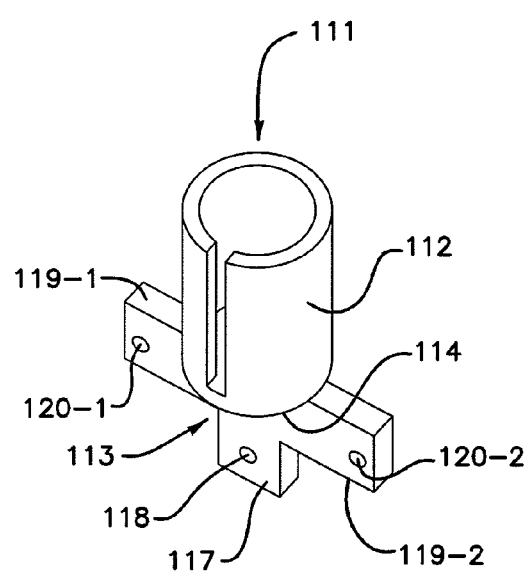
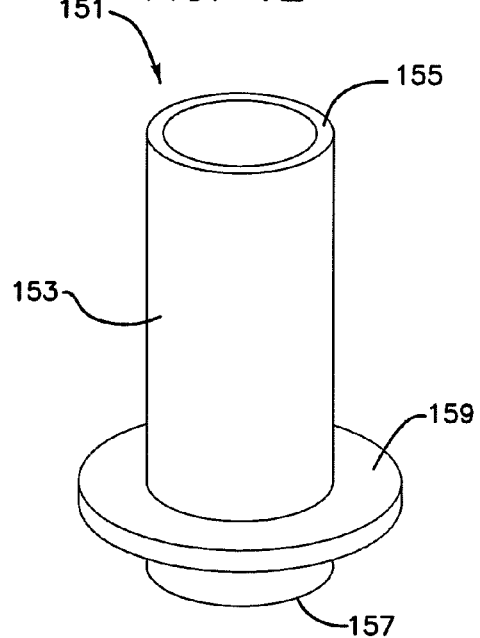

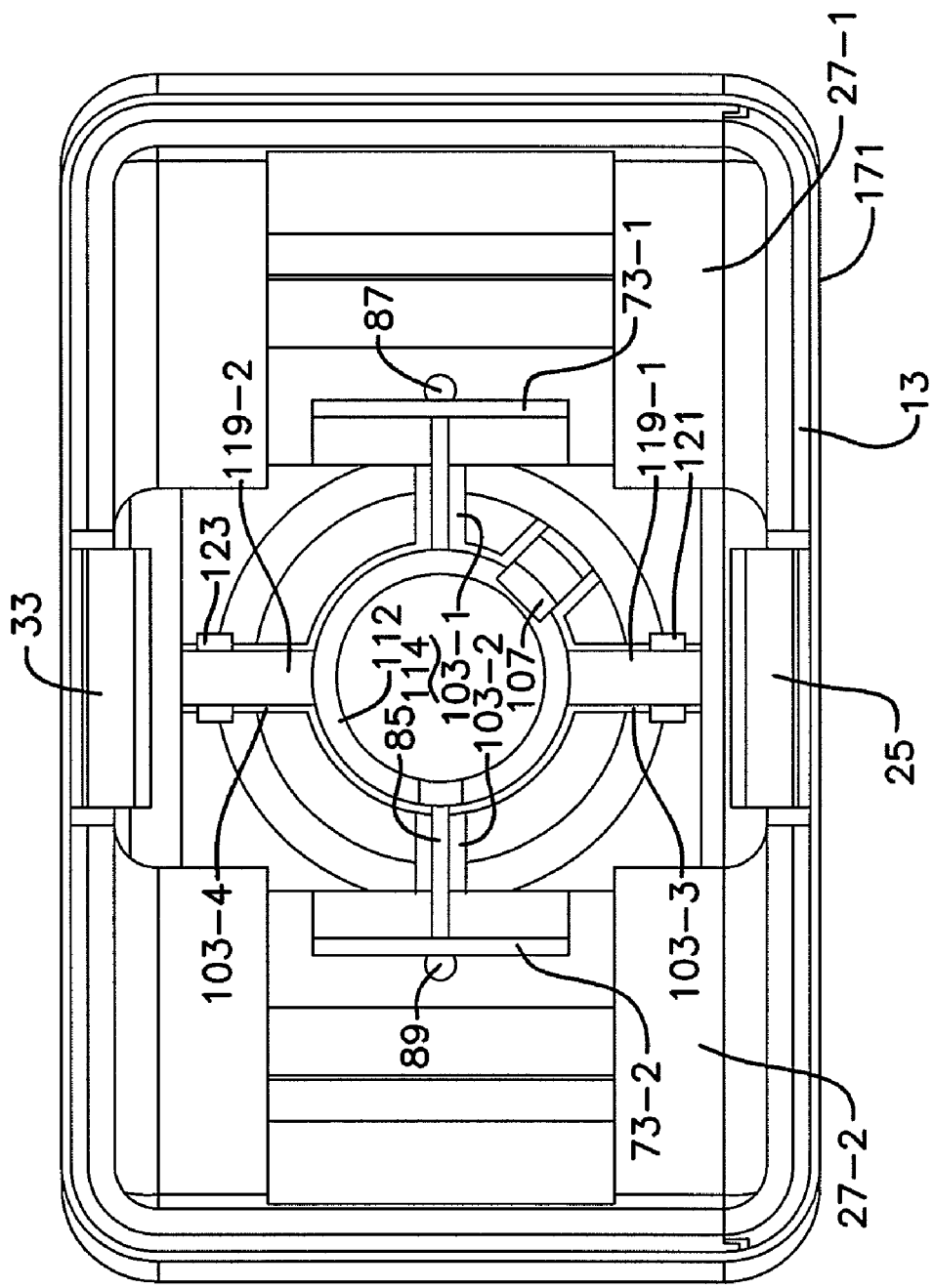

LANCET DEVICE

This application is a continuation application of Ser. No. 10/447,578, filed on May 29, 2003, now U.S. Pat. No. 7,303,573, which are incorporated herein by reference.

BACKGROUND OF THE INVENTION

The present invention relates generally to lancet devices and relates more particularly to a novel lancet device.

There are many medical conditions for which it is desirable to draw a blood sample from a patient for analysis. For example, in the case of certain communicable diseases, a blood sample drawn from a patient may be analyzed for the presence of a blood borne pathogen. Alternatively, in the case of diabetes, blood samples drawn periodically from a patient may be used to monitor blood sugar levels.

Blood samples taken from a patient for blood sugar monitoring are typically obtained by piercing the skin of the patient using a lancet device. A lancet device typically includes a body and a lancet. The body is typically adapted to be held by the user, the lancet being coupled to the body and being adapted to pierce the skin of the patient so as to draw blood therefrom. In some lancet devices, the lancet extends from the body at all times. As can readily be appreciated, such lancet devices may inadvertently prick people and/or become contaminated with foreign objects and, therefore, pose a safety risk. Accordingly, in other lancet devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with such force that contact of the moving lancet tip with the skin of a patient results in the piercing of the skin of the patient. In many such lancet devices having a movable lancet, the lancet is automatically drawn back into the body after reaching its extended position in order to minimize the risk of inadvertent lancet sticks.

Lancet devices having a movable lancet typically fall into one of two types. In one such type of device, the lancet is, prior to use and without any prepping by a user, maintained in an armed state, ready to be fired. The firing of a lancet in such a device is typically effected either by pressing or compressing the entire device against the skin of the patient or by depressing a movable plunger or trigger on the device while holding the remainder of the device against the skin of the patient. Examples of the aforementioned type of lancet device are disclosed in the following documents, all of which are incorporated herein by reference: U.S. Pat. No. 5,201,324, inventor Swierezek, issued Apr. 13, 1993; U.S. Pat. No. 5,540,709, inventor Ramel, issued Jul. 30, 1996; U.S. Pat. No. 5,709,699, inventor Warner, issued Jan. 20, 1998; U.S. Pat. No. 5,755,733, inventor Morita, issued May 26, 1998; U.S. Pat. No. 6,322,574, inventors Lloyd et al., issued Nov. 27, 2001; U.S. Pat. No. 6,358,265, inventors Thorne, Jr. et al., issued Mar. 19, 2002; and U.S. Patent Application Publication No. US 2002/0087180, inventors Searle et al., published Jul. 4, 2002.

One drawback to lancet devices of the type described above is that such devices require the user, who is typically also the patient whose skin is about to be pricked, to provide the necessary force to drive the lancet through the skin of the patient. Because most people have an aversion to being pricked, there is a natural tendency for the patient to flinch before or as the lancet is moving, with the result that a clean piercing is often not achieved. Moreover, because an inexperienced patient often will not know the appropriate amount of force necessary to drive the lancet through the skin, it is not uncommon for such a patient to fail to insert the lancet through the skin, with the result that the procedure must be repeated.

Another drawback to lancet devices of the type described above is that it is possible for the lancet to be fired prematurely simply by the inadvertent application of pressure to the lancet device. As can readily be appreciated, the premature firing of the lancet may result in an undesired piercing of a person and/or in the contamination of the lancet. In addition, with respect to those lancet devices that also include a safety feature for preventing the lancet from being used multiple times, the premature firing of the lancet will prevent the lancet device from later being used for its intended purpose. Furthermore, for those lancet devices that do not include a safety feature for preventing the lancet from being used multiple times, even if the lancet is not fired prematurely and is, in fact, used on its intended patient, there is a risk that subsequent handling of the lancet device by a second person may result in an inadvertent lancet stick of said second person.

The second type of lancet device having a movable lancet typically takes the form of a pen-shaped device comprising a spring-loaded lancet, cocking means for storing energy in the spring, and trigger means for releasing the energy stored in the spring to drive movement of the lancet. In use, the spring is cocked, the device is held against the skin of the patient, and the trigger is fired. Examples of the aforementioned type of lancet device are disclosed in the following documents, all of which are incorporated herein by reference: U.S. Pat. No. 4,462,405, inventor Ehrlich, issued Jul. 31, 1984; U.S. Pat. No. 4,503,856, inventor Cornell et al., issued Mar. 12, 1985; U.S. Reissue Pat. No. 32,922, inventors Levin et al., reissued May 16, 1989; U.S. Pat. No. 5,613,978, inventor Harding, issued Mar. 25, 1997; and U.S. Patent Application Publication No. US 2001/0027326, inventor Schraga, published Oct. 4, 2001.

Of the above documents, U.S. Reissue Pat. No. 32,922 is illustrative. In this patent, there is disclosed a lancet device comprising an inner tubular member and an outer tubular member, the inner tubular member being telescopically mounted within the outer tubular member. A lancet holder is slidably mounted within the inner tubular member, the lancet holder receiving at its forward end a lancet. A shaft extends rearwardly from the lancet holder, the shaft traveling through the inner tubular member and terminating within the outer tubular member. A spring is mounted on the shaft within the inner tubular member, the spring biasing the lancet holder forwardly. A finger formed on the lancet holder is adapted to extend radially outwardly through a transverse opening in the inner tubular member. A trigger mounted externally to the inner tubular member is adapted to engage the lancet holder finger and to push said finger into the inner tubular member through the transverse opening. To cock the device, the outer tubular member is pulled away from the inner tubular member and then released. The pulling away of the outer tubular member causes the shaft to be pulled rearwardly and the spring to be compressed. In addition, the pulling away of the outer tubular member causes the finger on the lancet holder to be drawn into the transverse opening in the inner tubular member, thereby retaining the spring in its compressed state. To fire the device, the trigger is depressed. Depression of the trigger causes the finger to be pushed back into the inner tubular member, thereby releasing the spring. Said release of the spring results in the lancet being driven forwardly through the end of the inner tubular member. After firing, a second spring, which is located in the outer tubular member surrounding the rear end of the shaft, draws the lancet back into the inner tubular member.

One drawback to the aforementioned lancet device is that one must use two hands to cock the device, one hand to hold the inner tubular member and the other hand to pull the outer tubular member rearwardly relative to the inner tubular member. In addition, after cocking the device, one must re-position the hand that is going to be used to fire the device so that a finger is positioned over the trigger.

Another drawback to the aforementioned lancet device and to many of the other lancet devices described above is that such devices are intended to be used to prick the finger tip of a patient (the finger tip being highly vascularized) and then to have the patient express a drop of blood from the pricked finger tip. This can be problematic, however, since the finger tip has a high concentration of pain receptors located therein. Consequently, both the act of pricking the finger tip and the act of expressing blood therefrom can be quite painful. Moreover, this effect is magnified where the patient is diabetic, and frequent blood samples must be drawn. This problem cannot simply be avoided by using the same devices on alternate body parts, such as the forearm, the trunk, the buttocks and the upper thighs, which do not have as high a concentration of pain receptors as the finger tips, since these devices are not designed to draw an adequate amount of blood for sampling from these less vascularized body parts.

SUMMARY OF THE INVENTION

It is an object of the present invention to provide a novel lancet device.

It is another object of the present invention to provide a lancet device as described above that overcomes at least some of the drawbacks associated with existing lancet devices.

It is still another object of the present invention to provide a device as described above that can be mass-produced relatively inexpensively, that has a minimal number of parts, and that is easy to operate.

In furtherance of the above and other objects to be described or to become apparent from the description below, there is provided, according to one aspect of the invention, a lancet device comprising (a) a body, said body comprising an open top end and at least one side opening; (b) a spring, said spring being mounted in said body and being transformable between a cocked state of comparatively greater compression and an uncocked state of comparatively lesser compression, said spring being manually accessible for compression through said at least one side opening; and (c) a lancet, said lancet having a lancet tip, said lancet being coupled to said spring for movement between a retracted position wherein said lancet tip is positioned below said open top end of said body and an extended position wherein said lancet tip is positioned above said open top end of said body, said lancet being in said retracted position when said spring is in said cocked state and in said extended position when said spring is in said uncocked state.

According to another aspect of the invention, there is provided a lancet device comprising (a) a body, said body comprising an open top end; (b) a spring, said spring being mounted in said body and being reversibly transformable between a cocked state of comparatively greater compression and an uncocked state of comparatively lesser compression; (c) a lancet, said lancet having a lancet tip, said lancet being coupled to said spring for movement between a retracted position wherein said lancet tip is positioned below said open top end of said body and an extended position wherein said lancet tip is positioned above said open top end of said body, said lancet being in said retracted position when said spring is in said cocked state and in said extended position when said spring is in said uncocked state; (d) a releasable catch for retaining said spring in said cocked state; and (e) an actuator engageable with said releasable catch for releasing said releasable catch, said actuator being actuated by contact with the body part to be lanced by said lancet.

According to yet another aspect of the invention, there is provided a lancet device comprising (a) a body, said body comprising a tubular member terminating in an open top end; (b) a lancet, said lancet having a lancet tip, said lancet being movable from a retracted position wherein said lancet tip is positioned below said open top end of said tubular member to an extended position wherein said lancet tip is positioned above said open top end of said tubular member; (c) a spring, said spring being mounted in said body and being coupled to said lancet for moving said lancet from said retracted position to said extended position; (d) a releasable catch for retaining said lancet in said retracted position; (e) an actuator engageable with said releasable catch for releasing said releasable catch, said actuator extending through said open top end of said tubular member and being actuated by contact with the body part to be lanced by said lancet; and (f) a flexible seal for stretching the skin to be pierced by said lancet, said flexible seal being mounted on said tubular member and extending beyond said open top end.

According to still yet another aspect of the invention, there is provided a lancet device comprising (a) a body, said body comprising (i) a base, said base having an inner cavity and comprising a front, a back, a left side, a right side, a bottom and an open top, each of said left side and said right side including a scalloped portion having a longitudinal slot, and (ii) a hollow cover, said hollow cover being mounted on said base and comprising a bottom portion and a tubular top portion, said tubular top portion having an open top end and an open bottom end; (b) a spring, said spring being a generally U-shaped member mounted in said body and comprising a first outwardly biasing arm and a second outwardly biasing arm, said first outwardly biasing arm being accessible through said longitudinal slot in said left side of said base for compression towards said second outwardly biasing arm, said second outwardly biasing arm being accessible through said longitudinal slot in said right side of said base for compression towards said first outwardly biasing arm; (c) a lancet holder; (d) a support member, said support member being mounted in said base and comprising a cylindrical member, said cylindrical member comprising a longitudinally-extending bore aligned with said tubular top portion of said cover, said lancet holder being slidably mounted in said longitudinally-extending bore, said cylindrical member further comprising a catch, said catch being releasably engageable with said lancet holder when said spring is sufficiently compressed; (e) a lancet, said lancet being mounted in said lancet holder and having a lancet tip, said lancet being coupled to said spring for movement between a retracted position wherein said lancet tip is positioned below said open top end of said tubular top portion of said hollow cover and an extended position wherein said lancet tip is positioned above said open top end of said tubular top portion of said hollow cover, said lancet being in said retracted position when said spring is in a cocked state and in said extended position when said spring is in an uncocked state; (f) means for coupling said spring to said lancet holder; (g) means for biasing said lancet holder downwardly, said biasing means being weaker than said spring; (h) an actuator slidably mounted within said tubular top portion of said hollow cover and engageable with said catch for releasing said catch from said lancet holder, said actuator being actuated by contact with the body part to be lanced by said lancet; and (i) means for biasing said actuator away from said catch.

For purposes of the present specification and claims, various relational terms like "top," "bottom," "proximal," "distal," "upper," "lower," "front," and "rear" are used to describe the present invention when said invention is positioned in a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration an embodiment for practicing the invention. This embodiment will be described in sufficient detail to enable those skilled in the art to practice the invention, and it is to be understood that other embodiments may be utilized and that structural or mechanical changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate a preferred embodiment of the invention and, together with the description, serve to explain the principles of the invention. In the drawings wherein like reference numerals represent like parts:

FIG. 10 is an enlarged perspective view of the support member of the device of FIG. 1;

FIG. 11 is an enlarged perspective view of the lancet holder of the device of FIG. 1;

FIG. 12 is an enlarged perspective view of the actuator of the device of FIG. 1;

FIG. 15 is a top view of the cocked lancet device shown in FIG. 13, with the cover, the actuating mechanism, and the seal not being shown to illustrate the releasable restraint of the lancet holder by the releasable pawl.

DETAILED DESCRIPTION OF PREFERRED EMBODIMENTS

Figure 1:
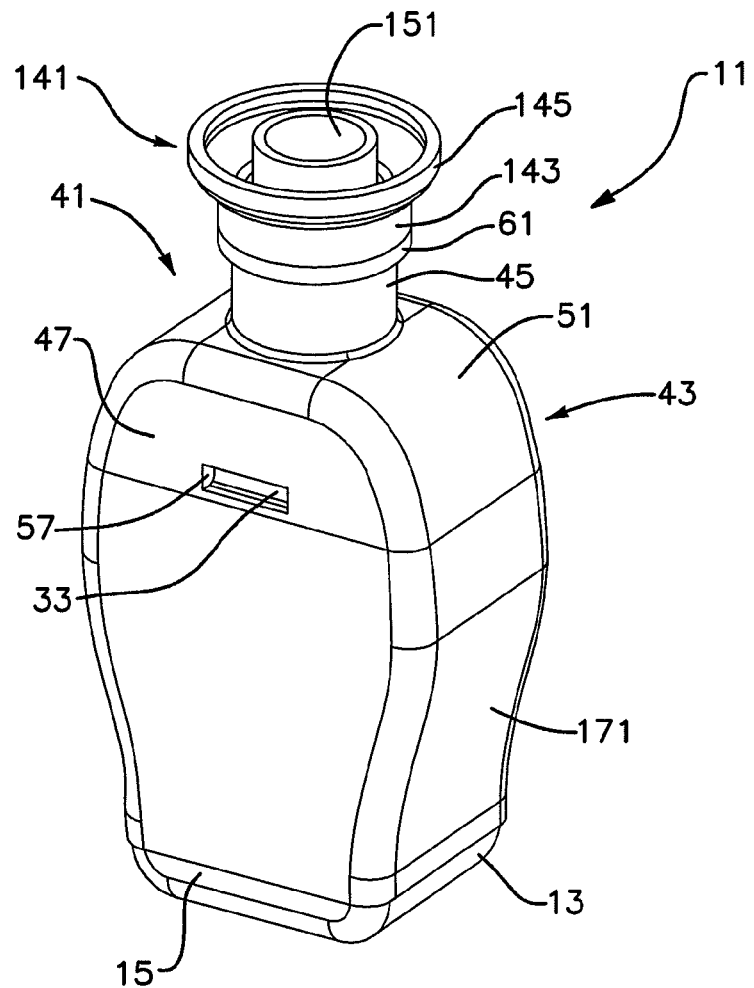
FIG. 1 is a perspective view of one embodiment of a lancet device constructed according to the teachings of the present invention, the lancet device being shown prior to being cocked.
Figure 3:
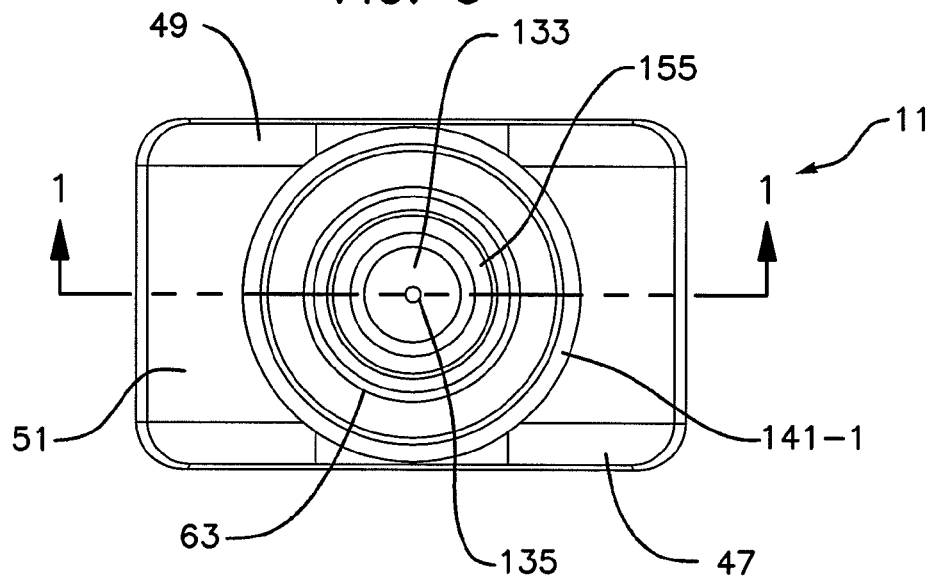
FIG. 3 is a top view of the uncocked lancet device shown in FIG. 1.
Figure 2:
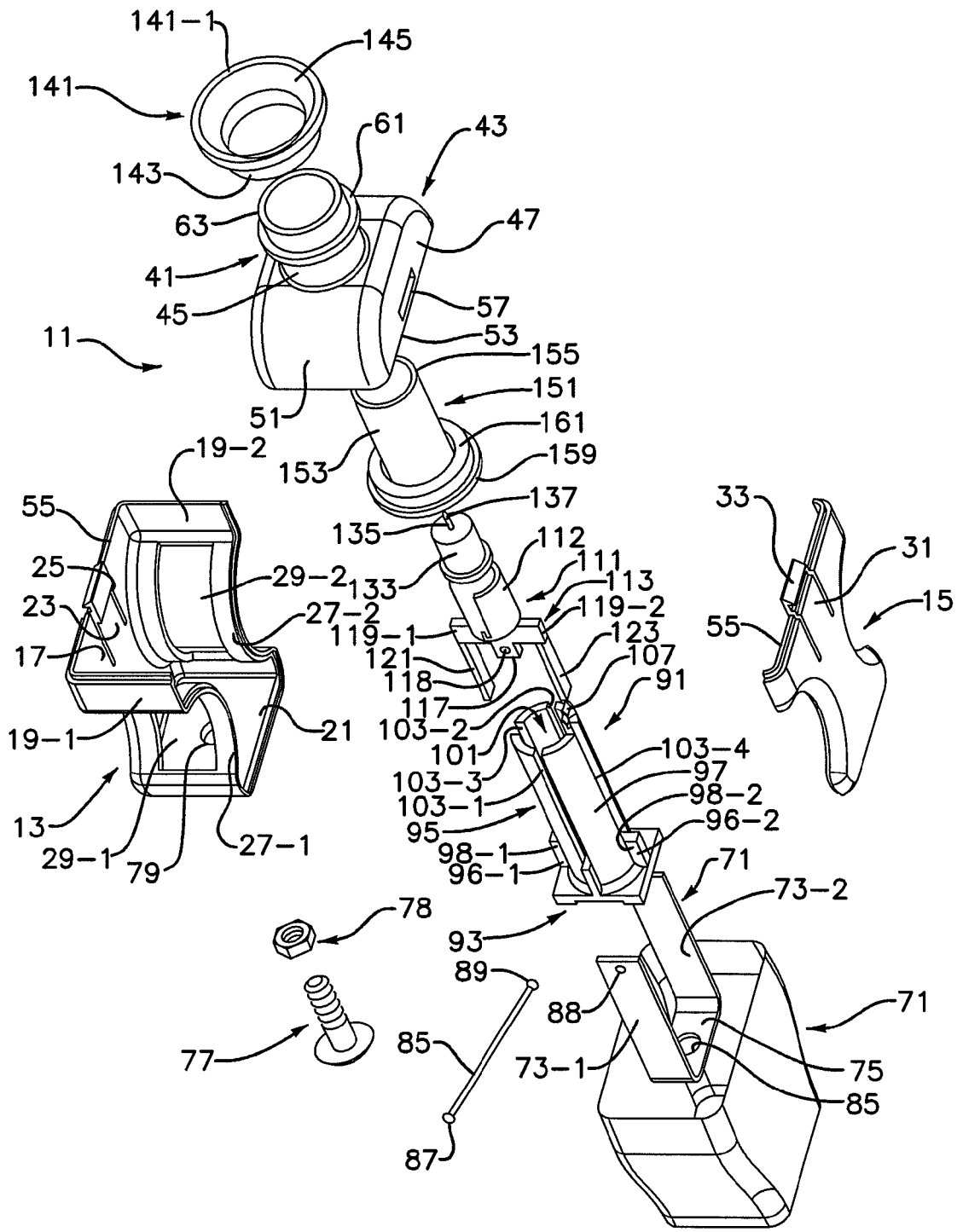
FIG. 2 is a partially exploded perspective view of the uncocked lancet device shown in FIG. 1.
Figure 4:
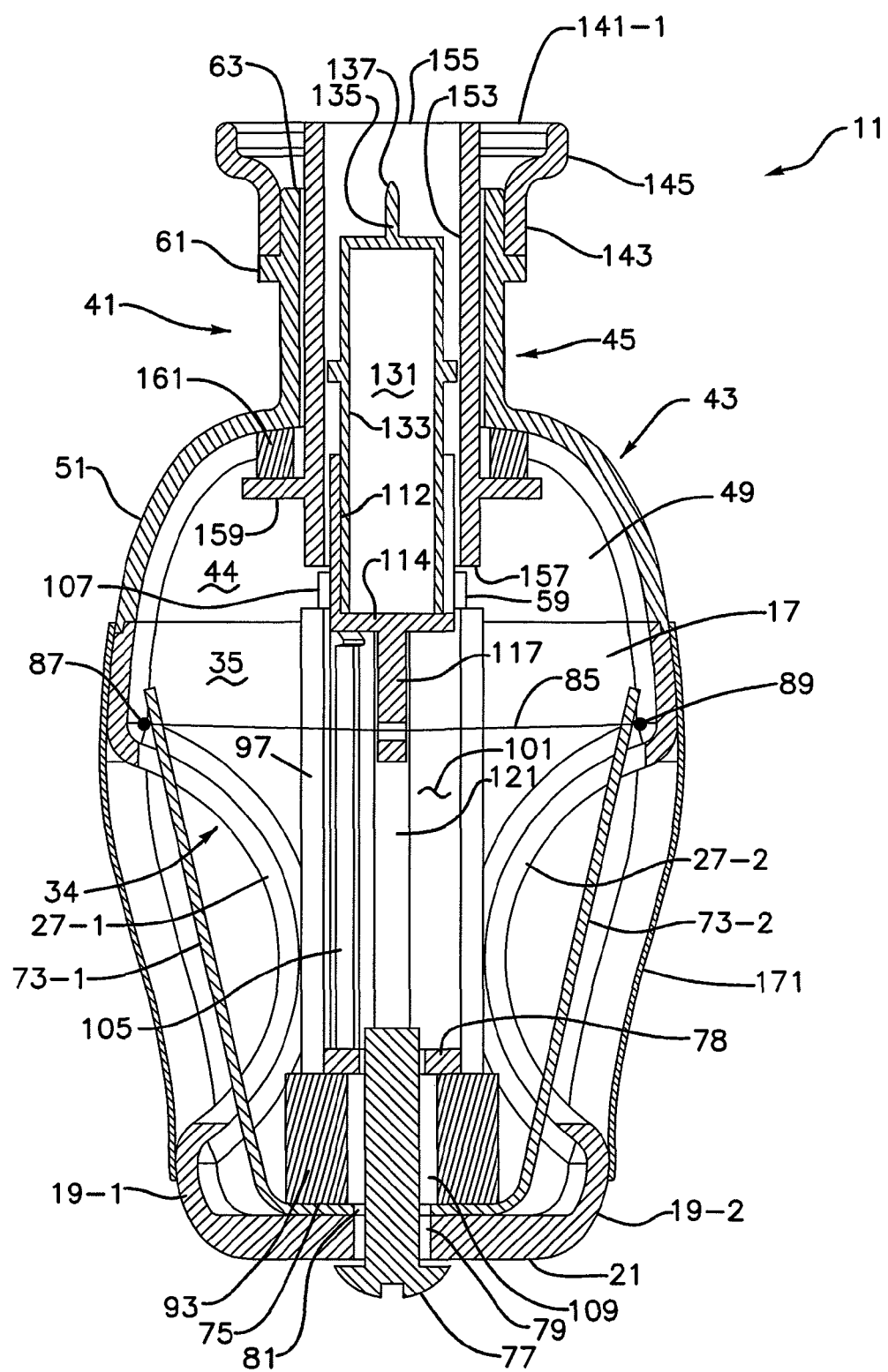
FIG. 4 is an enlarged longitudinal section view of the uncocked lancet device taken along line 1-1 of FIG. 3.
Figure 5:
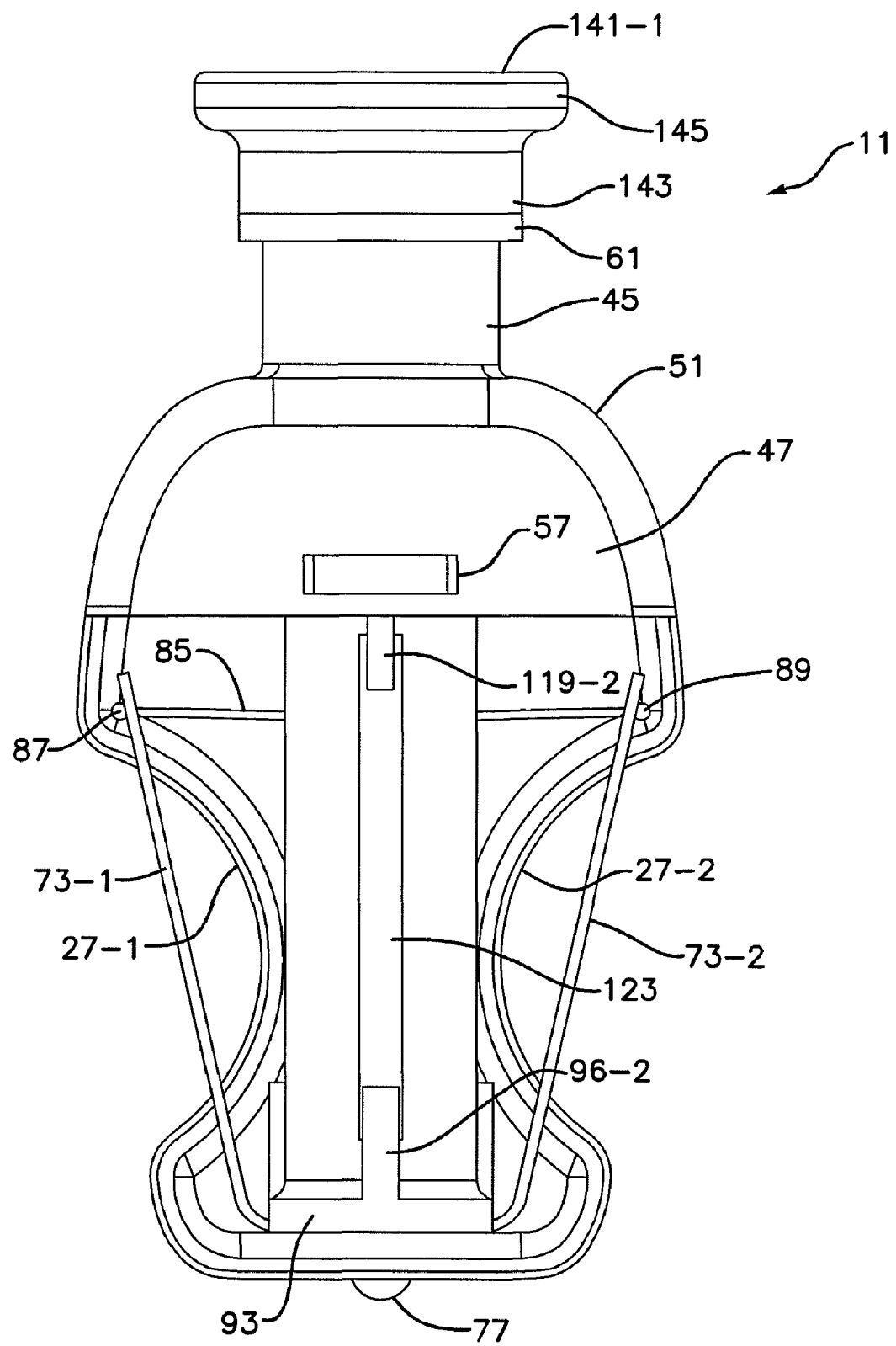
FIG. 5 is an enlarged front view of the uncocked lancet device shown in FIG. 1, with the front base portion and the skin not being shown.

Referring now to FIGS. 1 through 5, there are shown various views of one embodiment of a lancet device constructed according to the teachings of the present invention, said lancet device being shown in an uncocked state and being represented generally by reference numeral 11.

Figure 6:
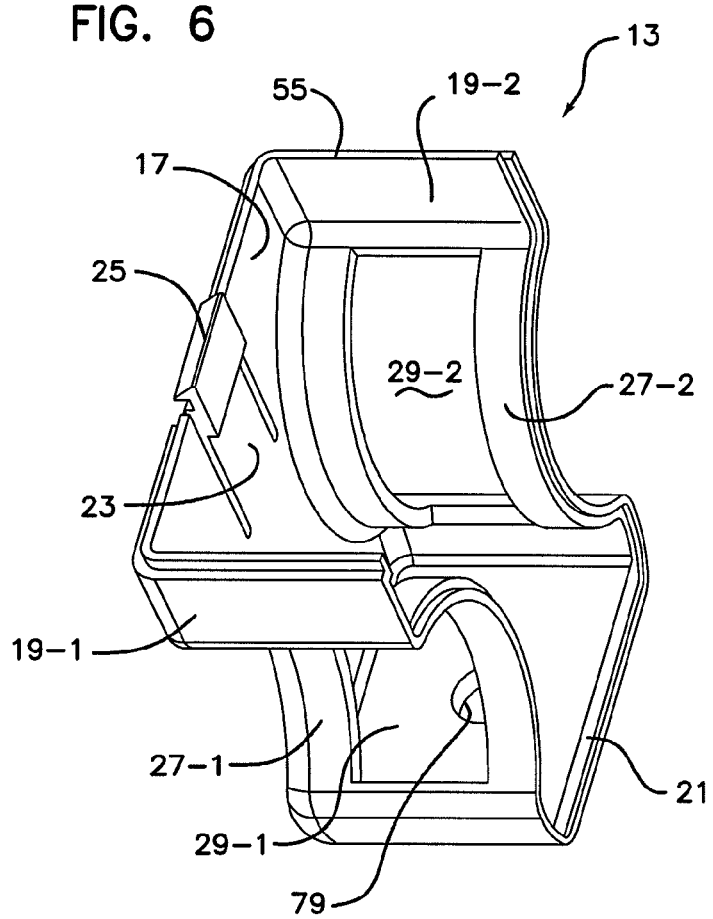
FIG. 6 is an enlarged perspective view of the rear base portion of the device of FIG. 1.

Device 11 includes a rear base portion 13 and a front base portion 15. Rear base portion 13, which is also shown separately in FIG. 6, is a unitary structure, preferably made of a durable molded plastic or similarly suitable material, and comprises a rear wall 17, a pair of side walls 19-1 and 19-2, a bottom wall 21, an open front and an open top. Rear wall 17 is shaped to include an upwardly extending tab 23, tab 23 terminating at its top end in a rearwardly facing pawl 25. For reasons to become apparent below, tab 23 is adapted to be resiliently flexed forwardly.

A scalloped portion 27-1 is provided in side wall 19-1, and a corresponding scalloped portion 27-2 is provided in side wall 19-2. As will be described below, scalloped portions 27-1 and 27-2 are adapted to receive a user's thumb and forefinger, respectively (or vice versa). Scalloped portion 27-1 is provided with a longitudinal slot 29-1, and scalloped portion 27-2 is provided with a corresponding longitudinal slot 29-2, the functions of slots 29-1 and 29-2 to become apparent below.

Figure 7:
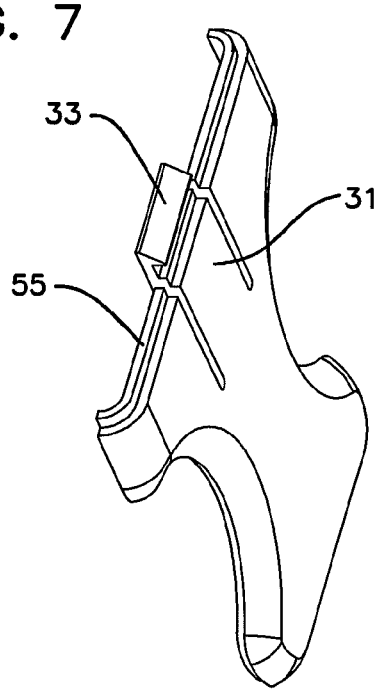
FIG. 7 is an enlarged perspective view of the front base portion of the device of FIG. 1.

Front base portion 15, which is also shown separately in FIG. 7, is a unitary structure, preferably made of the same material as rear base portion 13. Front base portion 15 has a shape that is substantially a mirror image of rear wall 17. As such, front base portion 15 is shaped to include an upwardly extending resilient tab 31, tab 31 terminating at its top end in an forwardly facing pawl 33. Front base portion 15 is fitted together with rear base portion 13, for example by mating peripheral edges, to jointly define a hollow base 34 having a base cavity 35.

Figure 8:
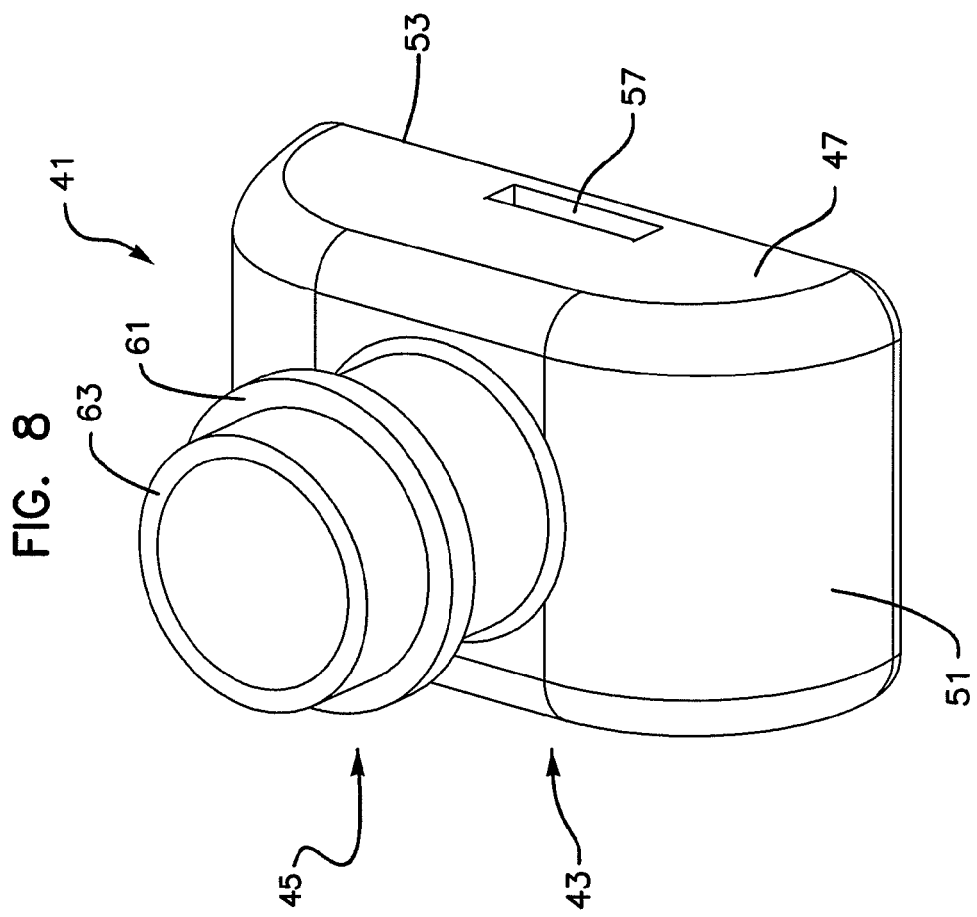
FIG. 8 is an enlarged perspective view of the cover of the device of FIG. 1.

Device 11 also includes a cover 41. Cover 41, which is also shown separately in FIG. 8, is a unitary structure, preferably made of a durable molded plastic or similarly suitable material, and comprises a bottom portion 43 and a top portion 45. Bottom portion 43, which is generally trough-shaped and defines an interior cavity 44, includes a front wall 47, a rear wall 49, an upwardly-curved intermediate wall 51 and an open bottom. Bottom portion 43 sits upon base 34, with the bottom edge 53 of bottom portion 43 being appropriately dimensioned to substantially match the top edge 55 of base 34. A transverse slot 57 is provided in front wall 47, and a corresponding transverse slot 59 is provided in rear wall 49, slot 57 receiving pawl 33 and slot 59 receiving pawl 25. In this manner, cover 41 is secured to base 34. To remove cover 41 from base 34, one flexes tab 31 rearwardly to remove pawl 33 from slot 57 and/or flexes tab 23 forwardly to remove pawl 25 from slot 59.

Top portion 45, which is generally tubular in shape and open at both ends, extends upwardly from intermediate wall 51. An external circumferential flange 61, the purpose of which will be described below, is provided on top portion 45 a short distance below its top end 63.

Base 34 and cover 41 jointly define a hollow body.

Figure 9:
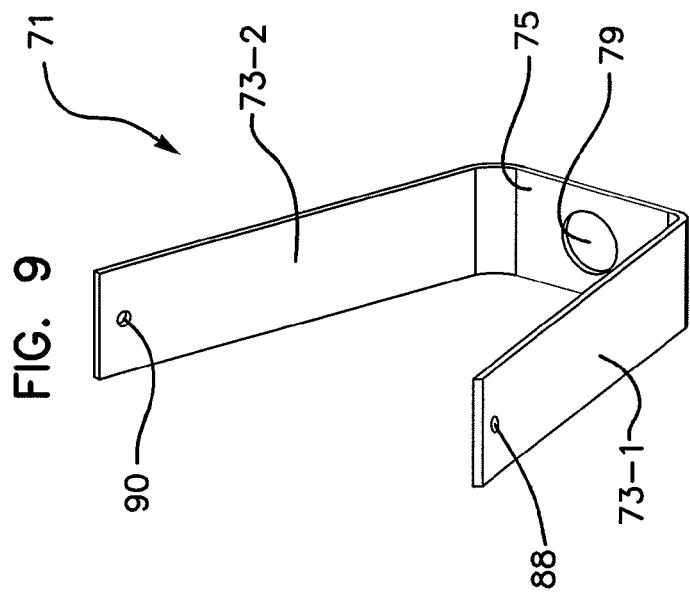
FIG. 9 is an enlarged perspective view of the biasing member of the device of FIG. 1.

Device 11 additionally comprises a biasing member 71 disposed within base 34. Biasing member 71, which is also shown separately in FIG. 9, is a unitary U-shaped ribbon-type structure, made of spring steel or the like, and comprises a pair of resilient, outwardly-biasing arms 73-1 and 73-2 interconnected by a base portion 75. Arms 73-1 and 73-2, the free ends of which are adapted to be pivoted towards one another by a user for reasons to become apparent below, are aligned with and accessible through slots 29-1 and 29-2, respectively. Base portion 75 is fixed to the top of bottom wall 21 of rear base portion 13 by a screw 77 and a nut 78, screw 77 being inserted through transverse openings 79 and 81 provided in bottom wall 21 and base portion 75, respectively.

Device 11 further comprises a flexible filament 85 disposed within base 34. Filament 85, which may be a length of string or another similarly suitable material, is a unitary structure having a first end 87 and a second end 89. First end 87 is inserted through a transverse opening 88 formed in arm 73-1 proximate to its free end, first end 87 being knotted to prevent its withdrawal through opening 88. Second end 89 is inserted through a transverse opening 90 formed in arm 73-2 proximate to its free end, second end 89 being knotted to prevent its withdrawal through opening 90. For reasons to become apparent below, the length of filament 85 is such that, when the free ends of arms 73-1 and 73-2 are pivoted towards one another (i.e., when device 11 is cocked), slack is created in filament 85, and when the free ends of arms 73-1 and 73-2 are nearly at their relaxed positions (i.e., when device 11 is uncocked), filament 85 is pulled taut.

It should be understood that, although biasing member 71 and filament 85 are described in the present embodiment as separate structures, biasing member 71 and filament 85 could be modified to be a unitary structure.

Device 11 also includes a support member 91. Support member 91, which is also shown separately in FIG. 10, is a unitary structure, made of a durable molded plastic or another similarly suitable material, and comprises a base portion 93 and a stem portion 95. Base portion 93, which is generally rectangular in shape, is seated on top of base portion 75 of biasing member 71.

Stem portion 95, which extends upwardly from base portion 93, is shaped to include a pair of tabs 96-1 and tabs 96-2 and a generally cylindrical member 97. Tabs 96-1 and 96-2 flank cylindrical member 97, with tab 96-1 facing rear wall 17 of rear base portion 13 and tab 96-2 facing front wall 15. For reasons to become apparent below, tab 96-1 is provided with a transverse opening 98-1, and tab 96-2 is provided with a transverse opening 98-2.

Cylindrical member 97, which is open at its top end, is shaped to include a longitudinally-extending bore 101 and a plurality of longitudinally-extending transverse slots 103-1, 103-2, 103-3 and 103-4 communicating with bore 101. Slots 103-1 and 103-2 are aligned with slots 29-1 and 29-2, respectively, of rear base portion 13 and permit filament 85 to pass through cylindrical member 97. For reasons to become apparent below, slot 103-3 is aligned with tab 96-1, and slot 103-4 is aligned with tab 96-2.

Cylindrical member 97 is also shaped to include an arm 105, arm 105 being biased radially inwardly towards bore 101. The top end of arm 105, which extends just beyond the top end of bore 101, is shaped to include a releasable catch or pawl 107, the purpose of which will be described below.

Support member 91 is fixed to biasing member 71 by screw 77 and nut 78, screw 77 being inserted through a bore 109 in support member 91 that is aligned with transverse openings 79 and 81 in bottom wall 21 and base portion 75, respectively. (Instead of being secured to one another by screw 77 and nut 78, support member 91 and biasing member 71 may be secured together by other means, such as by being molded together, by being coupled together by a snap feature, etc.)

Device 11 also includes a lancet holder 111, lancet holder 111 being slidably mounted in cylindrical member 97 of support 91. Lancet holder 111, which is also shown separately in FIG. 11, is a unitary structure, made of a durable molded plastic or another similarly suitable material, and comprises a top portion 112 and a bottom portion 113. Top portion 112 is a generally tubular structure having a closed bottom end 114 and an open top. Bottom portion 113, which is generally T-shaped, includes a downwardly extending central arm 117 and a pair of laterally extending side arms 119-1 and 119-2. Central arm 117, which is disposed within bore 101 of cylindrical member 97, is provided with a transverse opening 118 aligned with slots 103-1 and 103-2. For reasons to be described below, filament 85 extends through opening 118.

Side arm 119-1 extends through slot 103-3 and is provided with a transverse opening 120-1. One end of an elastic strap 121 is secured to arm 119-1, and the opposite end of strap 121 is secured to tab 96-1. Preferably, strap 121 is formed by overmolding (or "two-shot molding") a thermoplastic elastomeric ("TPE") material over arm 119-1 and through opening 120-1 and by overmolding (or "two-shot molding") the same TPE material over tab 96-1 and through opening 98-1. (Alternatively, instead of interconnecting arm 119-1 and tab 96-1 using strap 121, one could insert a first end of an elastic filament through opening 120-1 and insert a second end of said elastic filament through opening 98-1, said first and second ends of said elastic filament being knotted to prevent their withdrawal through opening 120-1 and opening 98-1, respectively.)

Side arm 119-2 extends through slot 103-4 and is provided with a transverse opening 120-2. One end of an elastic strap 123 is secured to arm 119-2, and the opposite end of strap 123 is secured to tab 96-2. Preferably, strap 123 is formed by overmolding (or "two-shot molding") a TPE material over arm 119-2 and through opening 120-2 and by overmolding (or "two-shot molding") the same TPE material over tab 96-2 and through opening 98-2. (Alternatively, instead of interconnecting arm 119-2 and tab 96-2 using strap 123, one could insert a first end of an elastic filament through opening 120-2 and insert a second end of said elastic filament through opening 98-2, said first and second ends of said filament being knotted to prevent their withdrawal through opening 120-2 and opening 98-2, respectively.)

Elastic straps 121 and 123 are used to bias lancet holder 111 downwardly; however, the biasing strength of biasing member 71 is greater than the biasing strength of straps 121 and 123. Accordingly, in the absence of a compressive or inwardly-directed force applied to biasing member 71 by a user, filament 85 is pulled taut by biasing member 71, causing holder 111 to be positioned at a relatively high position within support 91 and stretching straps 121 and 123 well beyond their normal or relaxed lengths (but not to their rupturing points). If, however, a compressive force is applied to biasing member 71 by a user, slack is created in filament 85, and straps 121 and 123 are permitted to contract towards their relaxed lengths, causing holder 111 to be pulled down within support 91. Once sufficient compressive force has been applied to biasing member 71 to draw the top of holder 111 down below pawl 107, further compressive force need not be applied to maintain biasing member 71 in a compressed state as pawl 107 pivots inwardly to engage the top of holder 111.

The energy stored in the thus compressed biasing member 71 may thereafter be released by removing pawl 107 from holder 111 in the manner to be described below. As can be appreciated, once the restraint on biasing member 71 is released, biasing member 71 expands towards its relaxed state, causing holder 111 to quickly move upwardly relative to support 91. Elastic straps 121 and 123, which are then highly stretched by the quick upward movement of holder 111, provide a small degree of downward spring to holder 111.

Device 11 additionally includes a lancet 131. Lancet 131, which may be a conventional, disposable lancet, is a unitary member, preferably made of metal or another similarly suitable material. Lancet 131 comprises a cylindrical base 133 and a stem 135. Base 133 is removably received within top portion 112 of holder 111. Stem 135 of lancet 131 extends upwardly from base 133 and terminates in a sharp tip 137 adapted to pierce the skin of a patient.

Device 11 further includes a seal 141. Seal 141, which may be made of silicone rubber or a similarly suitable material, is a unitary structure comprising a lower portion 143 and an upper portion 145. Lower portion 143 is tubular in shape and is inserted over top portion 45 of cover 41, with the bottom edge of lower portion 143 resting upon flange 61 of top portion 45. Upper portion 145 extends beyond top portion 45 of cover 41 and flares outwardly for reasons to become apparent below.

Device 11 additionally includes an actuator 151, actuator 151 being slidably mounted within top portion 45 of cover 41. Actuator 151, which is also shown separately in FIG. 12, is a unitary structure, preferably made of a durable molded plastic or another similarly suitable material. Actuator 151 is shaped to include a cylindrical portion 153, cylindrical portion 153 having a top end 155 and a bottom end 157. Top end 155 is positioned at approximately the top edge 141-1 of seal 141, and bottom end 157 extends into bottom portion 43 of cover 41 and is aligned with and spaced a short distance above pawl 107, as well as the remainder of cylindrical member 97 of support 91.

An external circumferential flange 159 is formed on actuator 151 and is positioned a short distance from bottom end 157. A ring 161, which may be made of foam or a like material, is mounted on top of flange 159. The bottom surface of ring 161 is fixed at a first point to the top of flange 159 using a suitable adhesive (not shown), and the top surface of ring 161 is fixed at a second point, approximately 180 degrees from said first point, to the bottom surface of intermediate wall 51 of cover 41. In this manner, actuator 151 is biased upwardly by ring 161.

Device 11 further includes a protective membrane or skin 171 tightly fitted over base 34 (except for the bottom portion thereof) and the exposed portions of biasing member 71. Skin 171 is preferably made of a flexible, elastic material.

Figure 13:
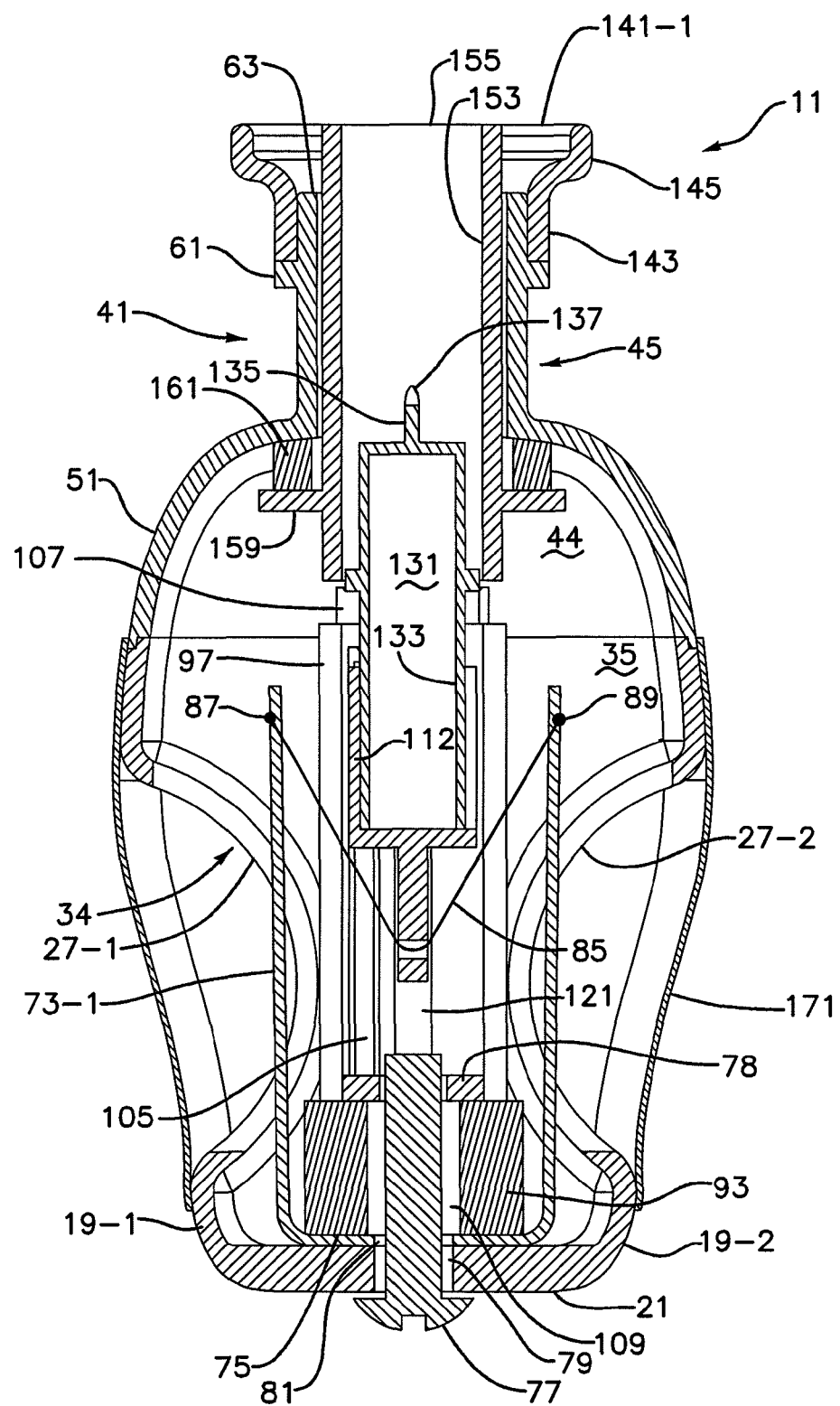
FIG. 13 is a longitudinal section view of the lancet device of FIG. 1, the lancet device being shown in a cocked state.
Figure 14:
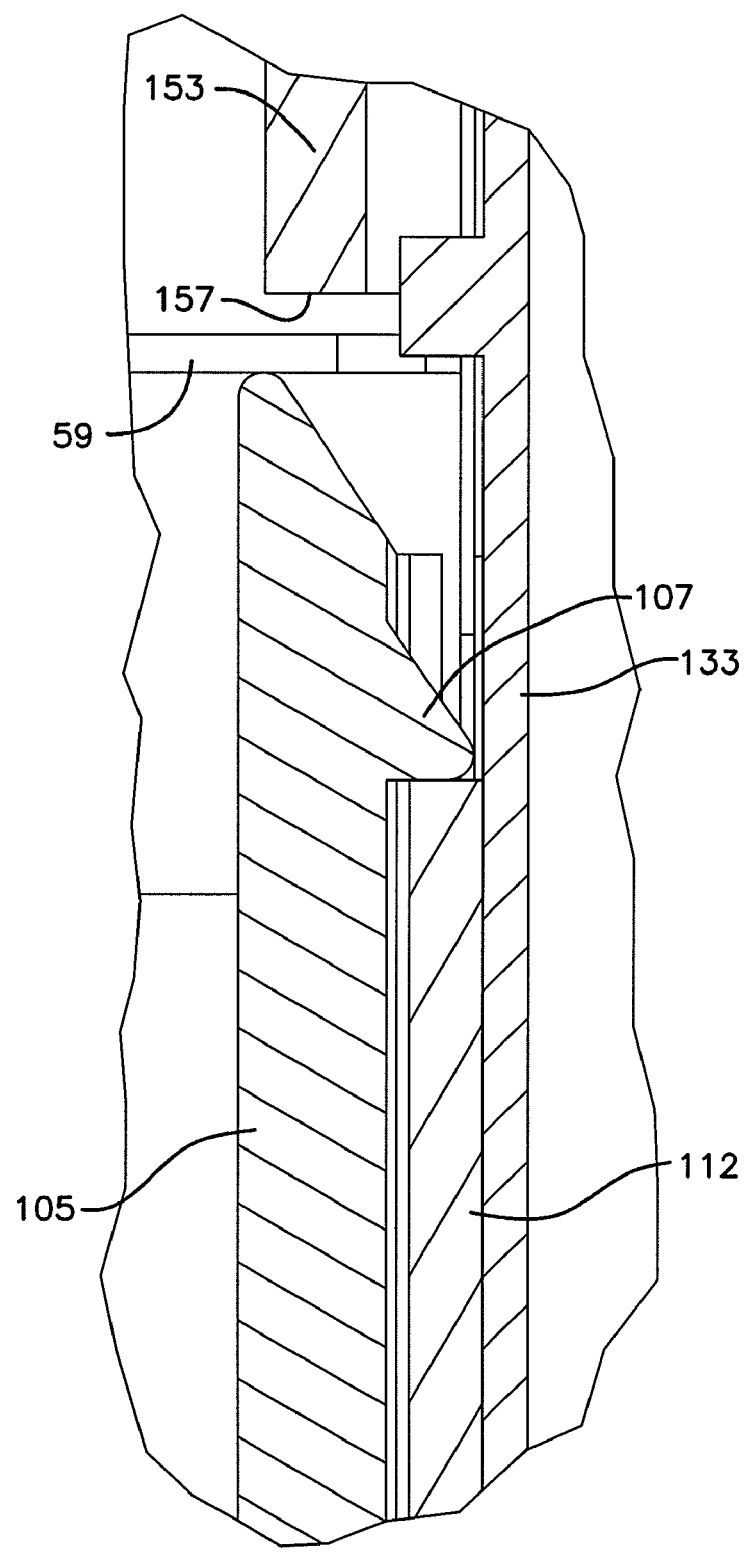
FIG. 14 is an enlarged fragmentary longitudinal section view of the cocked lancet device shown in FIG. 13, illustrating the releasable restraint of the lancet holder by the releasable pawl.

In use, an operator grips device 11 with the forefinger and the thumb of one hand, the forefinger being positioned against that portion of skin 171 covering scalloped portion 27-1 of base 34 and the thumb being positioned against that portion of skin 171 covering scalloped portion 27-2 of base 34 (or vice versa). At this point, prior to any cocking of device 11, device 11 is essentially as shown in FIGS. 1 through 5. The operator then cocks device 11 by compressing spring 71 with the forefinger and the thumb and then by releasing pressure from spring 71 while still maintaining a hold on device 11. As noted above, the compression of spring 71 causes the free ends of arms 73-1 and 73-2 to be pivoted towards one another and causes lancet holder 111 to be drawn down below pawl 107. The subsequent release of compression on spring 71 by the operator then causes lancet holder 111 to come into engagement with pawl 107, pawl 107 retaining holder 111 in place. At this point, device 11 is cocked and is essentially as seen in FIGS. 13 through 15. It can readily be appreciated that, with spring 71 thus restrained from returning to its relaxed state by the engagement of pawl 107 with holder 111, a considerable amount of potential energy is stored in spring 71. Device 11 is then used by pressing top edge 141-1 of seal 141 and top end 155 of actuator 151 against that portion of the patient where sampling is desired. As top edge 141-1 of seal 141 is pressed against the skin of the patient (and is engaged therewith), top edge 141-1 expands in diameter, stretching the engaged skin outwardly. Concurrently, as top end 155 of actuator 151 engages the skin of the patient, top end 155 causes distension of the skin and, at the same, causes actuator 151 to be moved downwardly. Continued movement of actuator 151 causes bottom end 157 of actuator 151 to move pawl 107 out of engagement with lancet holder 111, thereby resulting in the release of potential energy stored by spring 71 and the firing of lancet 131 into the patient.

Once device 11 has been used to pierce the skin of a patient, lancet 131 should be replaced. To access a used lancet 131 disposed within the body of device 11, a user depresses tabs 23 and/or 31 until cover 41 can be unhooked from base 34. The used lancet 131 may then be removed from holder 111 and replaced with a new lancet 131. After a new lancet 131 has been placed in holder 111, cover 41 may then be re-attached to base 34.

As noted above, one desirable property of device 11 is that device 11 is not limited to use on a finger but may be used on alternate sites of a patient.

In another embodiment (not shown), skin 171 is replaced with a rigid protective casing that encloses base 34 and the exposed portions of biasing member 71, the device further including a pair of depressable buttons, each button having a first end coupled to a respective arm 73 of biasing member 71 and a second end extending through the protective casing.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A lancet device comprising:
   (a) a body defining an interior space, a piercing aperture at a top end and opposing side openings;
   (b) a spring mounted within the interior space and being transformable between a cocked state of comparatively greater compression and an uncocked state of comparatively lesser compression, the spring configured to be transformable to the cocked state by pressure exerted on the opposing side openings;
   (c) a releasable catch for retaining the spring in the cocked state, the releasable catch being actuated by compression of the spring, and
   (d) an actuator engageable with the releasable catch for releasing the releasable catch.

2. The device of claim 1 further comprising:
   a lancet holder coupled to the spring, the lancet holder receiving the removable lancet so that a sharp tip of the removable lancet is positioned below the top end of the body in a retracted position and extending through the piercing aperture in an extended position, the removable lancet being in the retracted position when the spring is in the cocked state and in the extended position when the spring is in the uncocked state.

3. The device of claim 1 wherein the spring comprises a member having a pair of outwardly biasing arms compressed inwardly toward one another by the pressure exerted on the opposing side openings.

4. The device of claim 3 wherein the lancet holder is coupled to the spring with a filament secured at a first end to one of the outwardly biasing arms and at a second end to the other of the outwardly biasing arms and inserted through the lancet holder.

5. A lancet device for use with a removable lancet and operable with one hand, the device comprising:
   (a) a body having an open top end and two opposing side walls adapted to receive a user's thumb and forefinger;
   (b) a biasing member mounted within the body and having a base portion attached to the body and outwardly biasing arms connected by the base portion, a free end of each of the outwardly biasing arms configured to be pivoted toward one another to a cocked state by pressure on a flexible portion of each opposing side wall;
   (c) a releasable catch for retaining the outwardly biasing arms in the cocked state; and
   (d) an actuator engageable with the releasable catch for releasing the releasable catch.

6. The lancet device of claim 5 further comprising a flexible seal for stretching a skin of the user, the flexible seal being mounted on the body and extending beyond the open top end.

7. A method of using with one hand a lancet device with a removable lancet, the method comprising:
   (a) gripping a body having an open top end and opposing side walls each with a flexible portion with one hand, the open top end positioned toward a user when gripped;
   (b) cocking the device with the one hand by tightening the flexible portions of the opposing side walls with the grip and then releasing the grip while maintaining a hold on the device such that a spring is compressed, the spring being mounted within the body and having a base portion attached to the body and outwardly biasing arms connected by the base portion, a free end of each of the outwardly biasing arms configured to be pivoted toward one another and being compressed to cock the device wherein the spring is retained by a releasable catch; and
   (c) actuating the device by pressing the open top end against a skin of the user with the one hand, wherein an actuator engages the releasable catch releasing the spring to an uncocked position when the device is pressed against the skin.

8. The method of claim 7 further comprising stretching the user's skin with the open top end after actuating.

9. A method of using a lancet device, the method comprising:
   (a) gripping a hollow body defining an interior space, the hollow body comprising an open top end and opposing side openings and the interior space housing a lancet holder;
   (b) inserting a removable lancet into the lancet holder, the lancet holder configured to couple with a spring mounted within the interior space;
   (c) tightening the grip on the opposing side walls, wherein the tightened grip compresses the spring to a cocked state of comparatively greater compression from an uncocked state of comparatively lesser compression, the spring configured to be transformable to the cocked state by pressure exerted on the opposing side openings; and
   (d) pressing the open top end of the hollow body against a skin of a patient, wherein the pressing actuates a releasable catch, the releasable catch configured to retain the spring in the cocked state until actuating the catch, which releases the spring to the uncocked state.

10. The method of claim 9 further comprising stretching the skin of the patient with a flexible seal mounted on the hollow body and extending beyond the open top end.

11. The method of claim 9 further comprising biasing the lancet holder away from the open top end of the body.

12. The method of claim 11 further comprising a support fixed within the body, the releasable catch being a part of the support, wherein biasing the lancet holder comprises contracting an elastic strap having a first end secured to the lancet holder and a second end secured to a tab proximate to a bottom of the support.

13. The method of claim 9 wherein the lancet is in a retracted position when the spring is in the cocked state and in an extended position when the spring is in the uncocked state.

\* \* \* \* \*